US009970952B2

(12) United States Patent
Liu et al.

(10) Patent No.: US 9,970,952 B2
(45) Date of Patent: May 15, 2018

(54) APPARATUS AND METHOD FOR EXTRACTING BIOLOGICALLY ACTIVE SUBSTANCES THROUGH MAGNETIC BEADS METHOD

(71) Applicant: GENMAG BIOTECHNOLOGY CO., LTD., Changzhou, Jiangsu (CN)

(72) Inventors: Xinzhi Liu, Changzhou (CN); Zhifang Guo, Changzhou (CN); Haifeng Zhao, Changzhou (CN)

(73) Assignee: GENMAG BIOTECHNOLOGY CO., LTD., Changzhou, Jiangsu (CN)

( * ) Notice: Subject to any disclaimer, the term of this patent is extended or adjusted under 35 U.S.C. 154(b) by 281 days.

(21) Appl. No.: 14/905,218

(22) PCT Filed: Jul. 11, 2014

(86) PCT No.: PCT/CN2014/082093
§ 371 (c)(1),
(2) Date: Apr. 22, 2016

(87) PCT Pub. No.: WO2015/007188
PCT Pub. Date: Jan. 22, 2015

(65) Prior Publication Data
US 2016/0245834 A1 Aug. 25, 2016

(30) Foreign Application Priority Data

Jul. 16, 2013 (CN) .......................... 2013 1 0298604
Jul. 16, 2013 (CN) .......................... 2013 1 0298613

(51) Int. Cl.
*G01N 35/00* (2006.01)
*C12M 1/32* (2006.01)
(Continued)

(52) U.S. Cl.
CPC ......... *G01N 35/0098* (2013.01); *C12M 33/06* (2013.01); *C12N 15/1006* (2013.01);
(Continued)

(58) Field of Classification Search
CPC ..................... G01N 35/0098; C12N 15/1006
See application file for complete search history.

(56) References Cited

U.S. PATENT DOCUMENTS

| 5,158,895 A * | 10/1992 | Ashihara ................ G01N 33/53 |
|---|---|---|
| | | 422/65 |
| 6,409,925 B1 * | 6/2002 | Gombinsky ......... B01J 19/0046 |
| | | 209/224 |
| 2009/0220979 A1 * | 9/2009 | Davis ............... C01N 33/54333 |
| | | 435/6.13 |

FOREIGN PATENT DOCUMENTS

| CN | 2890059 Y | 4/2007 |
|---|---|---|
| CN | 101838609 A | 12/2008 |

(Continued)

OTHER PUBLICATIONS

International Search Report and Written Opinion for PCT/CN2014/082093 dated Oct. 14, 2014, with English translations.
(Continued)

*Primary Examiner* — Jill A Warden
*Assistant Examiner* — Matthew D Krcha
(74) *Attorney, Agent, or Firm* — Meng H. Pua; Foley & Lardner LLP

(57) ABSTRACT

The present invention provides an efficient apparatus for extracting biologically active substances through a magnetic particle method, comprising a magnetic needle, a magnetic needle moving mechanism, a sleeve and a sleeve moving mechanism and a vibration mechanism, a bracket, a positioning mechanism; the vibration mechanism is capable of generating vibrations to enable the sleeve moving mechanism to make upward and downward vibrations; wherein the
(Continued)

magnetic needle can vertically insert into and move out of the sleeve; the sleeve can vertically insert into and move out of a sample treatment area; and the vibration mechanism comprises a lever bar, a movable fulcrum and a rotary mechanism. The present invention further provides an instrument comprising the apparatus for extracting biologically active substances. The present invention further provides a method for extracting and purifying biologically active substances using the apparatus or the instrument for extracting biologically active substances. The vibration frequency and amplitude of the apparatus and the instrument can be optionally adjusted, and the range of adjustments for the amplitude is greatly extended, so the apparatus and the instrument exhibit such advantages as making only small noise and have a long service life.

19 Claims, 5 Drawing Sheets

(51) Int. Cl.
G01N 1/34 (2006.01)
C12N 15/10 (2006.01)
G01N 1/40 (2006.01)

(52) U.S. Cl.
CPC ............. *G01N 1/34* (2013.01); *G01N 1/4077* (2013.01); *G01N 2001/4038* (2013.01); *G01N 2035/00465* (2013.01)

(56) References Cited

FOREIGN PATENT DOCUMENTS

| | | |
|---|---|---|
| CN | 202011883 U | 10/2011 |
| CN | 102492603 | 6/2012 |
| CN | 203174103 U | 9/2013 |
| CN | 103805497 | 5/2014 |
| CN | 103805508 | 5/2014 |

OTHER PUBLICATIONS

Office Action for CN2013102986044 dated Dec. 24, 2015, with English translation.

* cited by examiner the present application claims priority of the Chinese

APPARATUS AND METHOD FOR EXTRACTING BIOLOGICALLY ACTIVE SUBSTANCES THROUGH MAGNETIC BEADS METHOD

The present application claims priority of the Chinese patent application numbered 201310298604.4 entitled Apparatus and Method for Extracting Biologically Active Substances through Magnetic Particle Method, filed on 16 Jul. 2013, and the Chinese patent application numbered 201310298613.3 entitled Instrument and Method for Extracting Biologically Active Substances through Magnetic particle Method. The disclosure of these applications is incorporated by reference in its entirety.

TECHNICAL FIELD

The present application relates to the technical field of biological instruments and apparatuses. Specifically, the present invention provides an automatic apparatus for extracting biologically active substances, and an instrument and a method for extracting biologically active substances using said apparatus.

BACKGROUND OF THE INVENTION

It is of significant importance to extract biologically active substances, for example, cells, proteins and nucleic acids in various areas such as modern clinical disease diagnosis, blood transfusion safety, forensic identification, surveillance of microorganism in environmental applications, food safety detection and molecular biology. Among these, nucleic acid, as a biologically active substance compound built by a plurality of nucleotides polymerized together, is one of the most essential substances for life. Nucleic acid can be widely found inside animal cells, plant cells, microorganisms and organisms. On the basis of different chemical compositions, nucleic acids may be categorized as ribonucleic acid (which is referred to as RNA for short) and deoxyribonucleic acid (which is referred to as DNA for short). DNA is the primary material base for storing, reproducing and transferring hereditary information, while RNA plays an important role in the process of protein synthesis. As biological technologies develop rapidly and the polymerase chain reaction (PCR) technique is widely applied in various areas, including disease diagnosis in medical industry, genetic modification detection in agriculture and many other areas, a method and an instrument for high-throughput extraction of biologically active substances from samples and for automatic extraction of biologically active substances are highly demanded.

It is a new technology that has been developed in recent years to extract biologically active substances, particularly, active macromolecules, through a magnetic particle method. The magnetic particle method refers to utilization of magnetic particles which are capable of recognizing specificity of cells, proteins or nucleic acids, and the magnetic particles can specifically combine with nucleic acid molecules, and thence separate active macromolecules from samples of blood, animal tissues, food, pathogenic microorganisms and the like under the effect of a magnetic field. For example, according to a principle same as the principle for silica spin column, extraction of a nucleic acid through magnetic particle method can fabricate superparamagnetic silicon oxide Nano-magnetic particles through making modification to the surface of superparamagnetic Nano-particles by means of Nano technology. The magnetic particles of this kind are capable of recognizing specificity of nucleic acid molecules. By means of the superparamagnetic nature of silicon dioxide Nano particles, DNA and RNA can be extracted from a sample in the presence of a chaotropic salt (e.g., guanidine hydrochloride, guanidinum thiocyanate, etc.) under the effect of an external magnetic field.

Automatic extraction instruments applying a magnetic particle method can be categorized into ones applying magnetic rod technique and ones applying suction process. The suction process is conducted by means of an automatic liquid transfer device. Take the nucleic acid extraction instrument through a magnetic particle method as an example, an automatic liquid transfer device may be used to add lysis buffer, and to attract magnetic particles; to suction a solution away, to add a rinsing liquid, to attract magnetic particles, to suction the rinsing liquid away, and to add an elution buffer solution. However, because the suction process is subject to a problem of retaining magnetic particles at the meantime of removing waste liquids, the liquid transfer device cannot be placed too close to magnetic particles; and this in turn affects the elution efficiency and purification.

Extraction through magnetic rod technique is a technology that has been developed in recent years and the working principle behind it is to immerse a magnetic separation device into a liquid so as to enable particles, which are capable of being magnetically attracted, in the mixture to aggregate on the surface of the separation device under the effect of a magnetic field. In one of the modes, the magnetic separation device is a sleeve, and insertion of a magnetic rod makes the sleeve magnetic and enables particles, which are capable of being magnetically attracted, in the mixture to aggregate on the surface of the sleeve; the sleeve is no longer magnetic when the magnetic rod is taken out from the sleeve, and thus the particles magnetically attracted then are separated from the surface of the sleeve. The through-put of a nucleic acid extraction instrument through magnetic rod technique is usually equipped with 8, 16, 32 or 96 channels; as compared with a suction process, the advantage of the magnetic rod technique is that there is no liquid residue at each step since the magnetic rod only takes magnetic particles and transfers the same into corresponding reaction wells at subsequent steps. The mechanism for moving the magnetic rod in an instrument applying the magnetic rod technique is capable of moving the rod upward and downward in the sleeve, which is favorable for operations of lysis, resining and purification in the extraction process.

SUMMARY OF THE INVENTION

The present invention provides an efficient automatic apparatus and instrument for extracting biologically active substances through the magnetic rod technique, which is applicable in various areas such as clinical disease diagnosis, blood transfusion safety, forensic identification, surveillance of microorganism in environmental applications, food safety detection and research of molecular biology, for the purposes of extracting and purifying biologically active substances, for example, cells, proteins and nucleic acids.

Specifically, the present invention provides an apparatus for extracting biologically active substances comprising: a magnetic needle 7 and a magnetic needle moving mechanism 6; the magnetic needle moving mechanism comprises a magnetic needle bracket and a magnetic needle lifting mechanism, and the magnetic needle is detachably secured onto the magnetic needle bracket, wherein the magnetic needle is capable of inserting into and moving out of a sleeve under upward and downward movements of the magnetic needle lifting mechanism;

a sleeve 4 and a sleeve moving mechanism 3; the sleeve moving mechanism comprises a sleeve bracket and a sleeve lifting mechanism; the sleeve is detachably secured onto the sleeve bracket; wherein, the sleeve is capable of inserting upright into and moving out of a sample treatment area under upward and downward movements of the sleeve lifting mechanism; in addition, the sleeve moving mechanism is capable of making upward and downward vibrations;

a bracket 13 for holding the magnetic needle moving mechanism 6 and the sleeve moving mechanism 3; and a vibration mechanism 19 capable of generating and outputting vibrations so as to enable the sleeve movement mechanism 16 to make upward and downward vibrations.

In one aspect of the present invention, the vibration mechanism is disposed above the bracket 13. The bracket may comprise supporting posts and a bracket ceiling. In such case, the vibration mechanism can be mounted on the top of the bracket ceiling.

In another aspect of the present invention, wherein the vibration mechanism comprises a lever bar, a movable fulcrum and a rotary mechanism, wherein the rotary mechanism comprises a wheel and an axis; when the rotary mechanism turns around its axis, the outer rim of its wheel can push the lever bar to rotate around the movable fulcrum thereby generating vibrations.

In one aspect, the apparatus provided by the present invention is characterized in that the arrangement of the lever bar, the movable fulcrum and the rotation mechanism allows the peak negative amplitude of vibrations output to the sleeve moving mechanism to keep unchanged regardless of any change to the amplitude of the vibrations generated by said vibration mechanism. Accordingly, no matter how the amplitude of the vibrations generated and output by the vibration mechanism changes, namely, no matter how the amplitude of the vibrations transmitted to the sleeve bracket changes, the peak negative amplitude of the vibrations of the sleeve of the apparatus provide by the present invention keeps unchanged.

The rotary mechanism in the vibration mechanism of the apparatus provided by the present invention comprises a wheel with lined outline of a specific style and an axis; when the rotary part thereof rotates around the axis, the outer rim of the wheel is capable of pushing the lever bar to turn around the movable fulcrum, thereby generating and outputting vibrations. In another aspect of the present invention, the rotary mechanism is an eccentric rotary mechanism, which means the axis of the rotary part is off the centre, namely, an eccentric rotary mechanism. The eccentric rotary mechanism may be an eccentric cam or the like.

In the present invention, the point, from which the distance from the outer rim of the outline of the rotary mechanism (particularly a eccentric rotary mechanism) to the axis is the shortest, is referred to as the closest outline point. In the present invention, the working state of the vibration mechanism refers to the state when the outer rim of the wheel of the vibration mechanism contacts and pushes the lever bar to turn around the lever fulcrum at the time the rotary mechanism of the vibration mechanism turns around the axis. In the present invention, when the closest outline point of the rotary mechanism in the vibration mechanism exerts a pushing force on the lever bar (usually refers to the moment when the closest outline point of the vibration mechanism comes into contact with the lever bar), the lever bar in the vibration mechanism turns around the lever fulcrum, and the position at which the lever bar turns around the lever fulcrum is referred to as the fulcrum position of peak negative amplitude. In an embodiment of the present invention, in the apparatus provided by the present invention, the lever bar, the movable fulcrum and the rotary mechanism of the vibration mechanism is so arranged that, under the working state, changes to the position of the movable fulcrum are restricted to the fulcrum position of the peak negative amplitude. Accordingly, no matter how the position of the lever bar changes under push from the rotary mechanism of the vibration mechanism, and no matter how the position of the movable fulcrum adjusts on the lever bar, namely, regardless of any change to the amplitude of the vibrations generated and output by the vibration mechanism, this arrangement enables the peak negative amplitude of vibrations output by the vibration mechanism to keep unchanged, thereby allowing the peak negative amplitude of vibration output to the sleeve moving mechanism to keep unchanged regardless of any change to the amplitude of the vibrations, namely, the peak negative amplitude of the vibrations of the sleeve of the apparatus provided by the present application keeps unchanged. In the apparatus of the present invention, the vibration mechanism is capable of outputting vibrations via a fix point on the lever bar, and the point like this is usually positioned on the other side of the fulcrum of the contact point between the rotary mechanism and the lever bar. No matter how the amplitude output to the sleeve bracket by the vibration mechanism changes, the negative peak of the amplitude at the fix point keeps unchanged, which thence allows the negative peak of the amplitude of the sleeve of the apparatus provide by the present invention to remain unchanged.

The rotary mechanism used in the present invention may be an eccentric rotary mechanism, which has an axis (i.e. rotating point) and a wheel of a specific style lined outline, and the axis is off the centre. Preferably, the rotary mechanism may use a disc as its wheel, namely an eccentric wheel. The use of a circular wheel has such advantages as easy to manufacture, simple to process and having vibrations with amplitudes easy to adjust. In addition, an eccentric cam with an axis off the centre also can be adopted as the eccentric rotary mechanism of the present invention.

A rotary mechanism with an axis in the centre and capable of generating vibrations can also be used in the present invention, for example, a cam with an elliptical rim.

In the present invention, the contact manner of the movable fulcrum and the lever bar can be that the fulcrum is in contact with the lower edge of the lever bar or a groove or a hollow slot embedded in the lever bar.

In an embodiment of the present invention, the movable fulcrum is multiple fulcrums capable of separating from or coming into contact with the lever bar individually, and can come into contact with the lever bar discretely so as to form a single fulcrum on the basis of needs in practice; accordingly, this makes it possible to generate vibrations with a specific amplitude. For example, it is viable to dispose under the lever bar or at the side of the lever bar a plurality of fulcrum blocks or fulcrum shafts capable of lifting or moving laterally, each of the fulcrum block or the fulcrum shaft can lift up to come into contact with the lower edge of the lever bar or move to insert into the lower edge of the lever bar or the groove, thereby each forming a fulcrum discretely.

In another embodiment of the present invention, the movable fulcrum is such a movable fulcrum that is capable of moving along the lower edge of the lever bar or along the groove or the hollow slot disposed on the lever bar, so as to enable generation of vibrations with constantly variable amplitudes. For example, the movable fulcrum is a fulcrum shaft mounted on a movable seat, and the fulcrum shaft gets into contact with the lower edge of the lever bar or is inserted into the groove or the hollow slot in the lever bar, and moves along the lever bar under the driving force of the movable seat to form a fulcrum.

The lever bar is preferably a linear lever bar. The lever bar can have a groove or a hallow groove parallel to its upper surface, which can be used for contacting with the fulcrum. The movable fulcrum can move along the edge of the lever bar (lower edge) or move inside the groove or the hollow slot disposed on the lever bar, and its moving direction is the axis direction of the lever bar. In this case, the vibration mechanism is so arranged that the minimum distance from the axis of the eccentric rotary mechanism to the outer edge of the rim is equal to the distance from the axis to the lever bar. In the case the eccentric rotary mechanism is an eccentric wheel, the vibration mechanism is so arranged that the minimum radius of the eccentric wheel (i.e. the minimum distance from the axis to the rim of the wheel) is equal to the distance from its axis to the lever bar. In this case, the radius direction of the minimum radius of the eccentric wheel is perpendicular to the moving direction of the movable fulcrum of the lever (i.e. the axis direction of the lever bar).

The lever bar also can be a folded or curved lever bar.

In another aspect of the present invention, the movable fulcrum comprises a moving bracket 23, a moving bracket driving mechanism 24 and a moving fulcrum axis 26; the lever bar has a hollow slot parallel to its upper surface, the moving fulcrum goes through the hollow slot and moves in the hollow slot under the driving force from the moving bracket driving mechanism, so as to form the movable fulcrum of the lever.

In one aspect of the present invention, the vibration outputting member of the vibration mechanism is a vibration wheel. In another aspect of the present invention, the lever bar has a vibration wheel 25, which may get into contact with the moving mechanisms for transmitting vibrations. The vibration wheel and the rotary mechanism are individually positioned on either side of the movable fulcrum.

In one aspect of the present invention, in the apparatus provided by the present invention, the magnetic needle bracket comprises a magnetic needle bracket end block 9 and a magnetic needle securing mechanism 8, wherein the magnetic needles are detachably secured onto the magnetic needle securing mechanism. The magnetic needle lifting mechanism comprises a magnetic needle propelling end block 17 disposed below the magnetic needle bracket block; when the magnetic needle propelling end block moves upward, it propels the magnetic needle bracket end block to move upward, thereby propelling the magnetic needle bracket to move upward.

In one aspect of the present invention, in the apparatus provided by the present invention, the sleeve bracket comprises a sleeve bracket end block 35 and a sleeve securing mechanism 5, wherein the sleeve is detachably secured onto the sleeve securing mechanism. The sleeve lifting mechanism comprises a sleeve lifting end block 36 disposed under the sleeve bracket end block 35; when the sleeve lifting end block moves upward, it pushes the sleeve bracket end block to move upward so as to push the sleeve bracket to go upward; when the lifting end block moves downward, the sleeve bracket end block makes synchronous downward movement with the sleeve lifting end block under the effect of gravity.

In one aspect of the present invention, in the apparatus provided by the present invention, the sleeve bracket is in contact with the vibration mechanism 19, so that the vibrations generated by the vibration mechanism allows the sleeve bracket to make upward and downward vibrations. In another aspect of the present invention, wherein the sleeve bracket end block of the sleeve bracket is in contact with the vibration wheel 25 of the vibration mechanism 19 for transmitting vibrations.

In one aspect of the present invention, the apparatus provided by the present invention comprises a bracket 13 for holding the magnetic needle moving mechanism and the sleeve moving mechanism. The bracket is capable of holding the magnetic needle moving mechanism and the sleeve moving mechanism of the apparatus provided by the present invention so as to enable them to be in a perpendicular and suspended state in the apparatus. The bracket may comprise supporting posts and a bracket ceiling.

In one aspect of the present invention, the vibration mechanism of the apparatus provided by the present invention is disposed above the mechanism bracket 13. For example, the vibration mechanism may be mounted on the top of the bracket ceiling 41 and is secured to the bracket ceiling 41 by means of screws or welding. Accordingly, when the magnetic needle moving mechanism 6 and the sleeve moving mechanism 5 move in the horizontal direction along the X axis and the Y axis, the vibration mechanism 19 makes synchronous movements. By the way of disposing the vibration mechanism above the mechanism bracket 13, the apparatus provide by the present invention exhibits such advantages as having a compact structure, easy maintenance, making only small noise, having a long service life and a lower manufacturing cost.

In one aspect of the present invention, the apparatus provided by the present invention has a positioning mechanism 14 that allows the magnetic needle moving mechanism 6 and the sleeve moving mechanism 3 to move in the horizontal direction along the X axis and the Y axis, in other words, a positioning mechanism 14 that allows the magnetic needle and the sleeve to move in the horizontal direction along the X axis and the Y axis.

The positioning mechanism 14 comprises an X axis positioning mechanism and a Y axis positioning mechanism.

In one aspect of the present invention, wherein the X axis positioning mechanism comprises an X axis bracket and an X axis movement driving mechanism.

In one aspect of the present invention, wherein the X axis movement driving mechanism 53 comprises an X axis movement motor 531, a linear rail 532, a lead screw 533 and a screw transmission member 534 connected with the bracket 13. Wherein the linear rail 532 can be disposed on the top of the X axis bracket 52. The bracket ceiling 41 of the bracket 13 is connected with the linear rail 532 through sliding fit. The screw transmission member 534 and the bracket 13 are secured.

In one aspect of the present invention, the Y axis positioning mechanism comprises a Y axis bracket and a Y axis movement driving mechanism 58.

In one aspect of the present invention, wherein the Y axis movement driving mechanism 53 comprises a Y axis movement motor 581, a Y axis movable sliding rail 582, a conveyor belt 583, an upper belt pulley 584 and a lower belt pulley, a connection slider 59 for establishing connection with the bracket 13, and a conveyor belt securing member 586 for fixed connection with the connection slider 59. Wherein, the sliding rail 582 is connected with the connection slider 59 through sliding fit. The conveyor belt 583 engages with teeth of the upper belt pulley 584 and the lower belt pulley.

In one aspect of the present invention, the magnetic needle in the apparatus provided by the present invention is made of a permanent magnet material.

In one aspect of the present invention, the sleeve in the apparatus provided by the present invention is made of a non-permanent magnet material.

The apparatus provided by the present invention are applicable for extraction of biologically active substances, for example, cells, proteins or nucleic acids.

The apparatus provided by the present invention can be used as an apparatus for extracting and purifying nucleic acids.

The present invention further provides an instrument comprising the aforementioned apparatus for extracting biologically active substances. The instrument comprises:
a housing,
a workbench on which a sample treatment area is disposed; and
the apparatus provided by the present invention for extracting biologically active substances.

Specifically, the instrument of the present invention can comprise:
a housing,
a workbench on which a sample treatment area is disposed;
a magnetic needle 7 and a magnetic needle moving mechanism 6, which comprises a magnetic needle bracket and a magnetic needle lifting mechanism; the magnetic needle is detachably secured onto the magnetic needle bracket; wherein the magnetic needle can vertically insert into and move out of the sleeve under the upward and downward movements of the magnetic needle lifting mechanism.
A sleeve 4 and a sleeve moving mechanism 3, which comprises a sleeve bracket and a sleeve lifting mechanism, and the sleeve is detachably secured onto the sleeve bracket; wherein the sleeve can be vertically insert into and move out of the sample treatment area under the upward and downward movements of the sleeve lifting mechanism; in addition, the sleeve moving mechanism can make upward and downward vibrations;
A bracket 13 for holding the magnetic needle moving mechanism 6 and the sleeve moving mechanism 3;
Optionally, a positioning mechanism 14 for allowing the magnetic needle moving mechanism 6 and the sleeve moving mechanism 3 to move in the horizontal direction along the X axis and the Y axis; and
a vibration mechanism 19 capable of generating and outputting vibrations so as to enable the sleeve moving mechanism 16 to make upward and downward vibrations.

In one aspect of the present invention, the vibration mechanism comprises a lever bar, a movable fulcrum and a rotary mechanism, wherein the rotary mechanism has a wheel and an axis; when the rotary mechanism turns around the axis, the outer rim of its wheel can push the lever bar to turn around the movable fulcrum so as to generate vibrations.

Wherein the bracket 13 comprises supporting posts and a bracket ceiling. The vibration mechanism is disposed above the bracket 13.

In one aspect of the present invention, in the instrument provided by the present invention, the workbench can be fixed or alternatively can be horizontally movable. Wherein the sample treatment area on the workbench can comprise a working area, a sample slot or sample cell, or a combination thereof. In a further aspect of the present invention, the sample treatment area has heating cells, under which a heater is configured.

The present invention further provides a method for extracting and purifying biologically active substances with the apparatus or instrument provided by the present invention. Wherein the biologically active substances can be cells, proteins or nucleic acids.

BRIEF DESCRIPTION OF THE DRAWINGS

Other additional features, aspects and advantages of the present invention are made more evident according to perusal of the following detailed description of exemplary embodiment(s) in conjunction with the appended drawings:

FIG. 3-1 illustrates a side cross-sectional schematic view of a preferred embodiment of the present invention;

FIG. 3-2 illustrates a side cross-sectional schematic view of a preferred embodiment of the present invention;

| Reference signs for the appended drawings | |
|---|---|
| 3 | Sleeve moving mechanism |
| 4 | sleeve |
| 5 | Sleeve securing mechanism |
| 6 | Magnetic needle moving mechanism |
| 7 | Magnetic needle |
| 8 | Magnetic needle securing mechanism |
| 9 | Magnetic needle bracket end block |
| 11 | Motor A |
| 12 | Motor B |
| 13 | Bracket |
| 14 | Positioning mechanism |
| 17 | Magnetic needle propelling end block |
| 19 | Vibration mechanism |
| 20 | Eccentric wheel driving motor |
| 21 | Eccentric wheel |
| 22 | Lever bar |
| 23 | Movable bracket |
| 24 | Movable bracket driving mechanism |
| 241 | Vibration mechanism movable bracket motor |
| 242 | Vibration mechanism linear rail |
| 243 | Vibration mechanism lead screw |
| 25 | Vibration wheel |
| 26 | Movable fulcrum shaft |
| 27 | Linkage A |
| 28 | Linkage B |
| 31 | Lead screw A |
| 32 | Lead screw B |
| 35 | Sleeve bracket end block |
| 351 | Protruding portion of the sleeve bracket end block |
| 352 | Bottom portion of the sleeve bracket end block |
| 36 | Sleeve lifting end block |
| 41 | Bracket ceiling |
| 42 | Supporting posts |
| 421 | Front securing block |
| 422 | Rear securing block |
| 4221 | Cuboid fixed block |
| 4222 | Cuboid fixed block |
| 4223 | Side wall of the supporting posts |
| 43 | Through-hole |
| 52 | X axis bracket |
| 53 | X axis movable driving mechanism |
| 531 | X axis movable motor |
| 532 | X axis movable linear rail |
| 533 | X axis movable lead screw |

-continued

| Reference signs for the appended drawings | |
|---|---|
| 534 | Nut transmission member |
| 54 | Roller |
| 56 | Y axis left bracket |
| 561 | Supporting panel A |
| 57 | Y axis right bracket |
| 571 | Supporting panel B |
| 572 | Sliding track |
| 58 | Y axis movement driving mechanism |
| 581 | Y axis movable motor |
| 582 | Y axis movable sliding rail |
| 583 | Conveyor belt |
| 584 | Upper belt pulley |
| 586 | Conveyor belt securing member |
| 59 | Connection slider |

DETAILED DESCRIPTION OF THE INVENTION

Here below, the present invention are to be described at length in conjunction with the appended drawings for a better understanding and description of the present invention.

Figure 1:
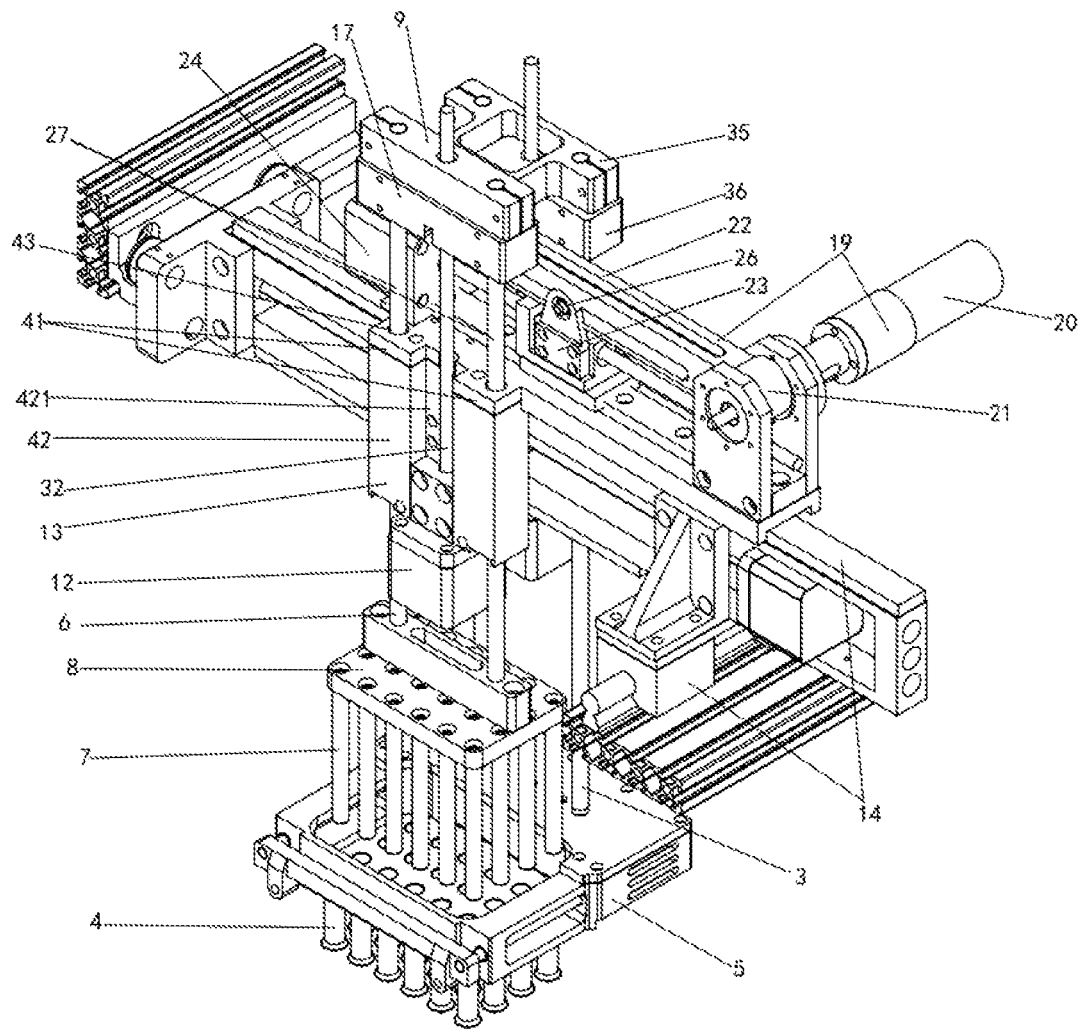
FIG. 1 illustrates a 3D view in the first direction according to a preferred embodiment of the present invention.
Figure 2:
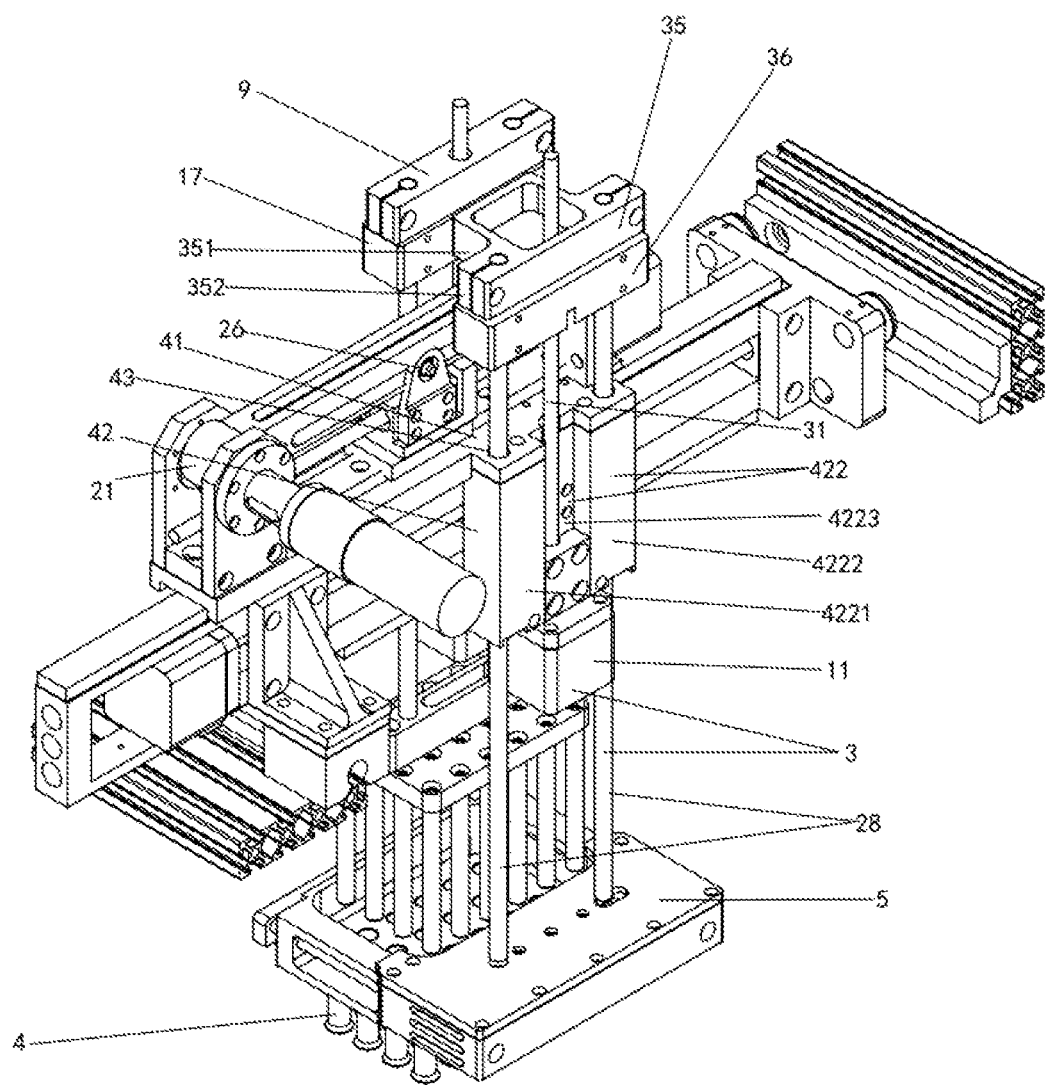
FIG. 2 illustrates a 3D view in the second direction according to a preferred embodiment of the present invention.

FIG. 1 shows a 3D view in the first direction of the inside of the apparatus and the instrument for extracting biologically active substances according to a preferred embodiment of the present invention. FIG. 2 illustrates a 3D view in the second direction of the apparatus and the instrument for extracting biologically active substances according to a preferred embodiment of the present invention.

The instrument provided by the present invention can be used for extracting and purifying nucleic acids. The instrument has a housing (not shown in the drawings), a workbench (not shown), a magnetic needle 7 and a magnetic moving mechanism 6, a sleeve 4 and a sleeve moving mechanism 3, a bracket 13 for supporting the magnetic needle moving mechanism and the sleeve moving mechanism, a positioning mechanism 14 for allowing the magnetic needle moving mechanism and the sleeve moving mechanism to move in the horizontal direction along the X axis and the Y axis, and a vibration mechanism 19 for generating vibrations and enabling the sleeve moving mechanism to vibrate upward and downward.

The housing (not shown) may comprise a ceiling, side panels and a bottom panel. The housing can isolate the instrument from the atmosphere to avoid contamination to samples and damage to parts of the instrument. The panel of the housing is usually made of a metallic material. The housing may have a sample window that can be opened and closed for placing in and taking out a sample. The housing can comprise an observation window made of a transparent material. The sample window and the observation window can be the same one. Additionally, the housing may have an external device interface for connecting with an external device, a display screen for displaying an operating interface, various operation switches, keys or buttons or the like. A bracket or a lateral beam may be further disposed inside the housing for supporting or holding the various mechanisms disposed inside the instrument.

The sleeve 4 is a tube with a closed bottom and a hollow chamber. The sleeve may be in the shape of, for example, a slim cylinder. The material for the sleeve is usually non-magnetic, for example, plastic. The selection for the material and the thickness of the sleeve and its design should not weaken the magnetic field or only slightly affect the magnetic field, but have to ensure that a magnetic field sufficient to attract magnetic particles or biological samples with magnetic particles is generated outside the sleeve at the time when the magnetic needle inserts into the sleeve.

The magnetic needle 7 can vertically insert into and move out of the sleeve. The bottom end of the magnetic needle (i.e. the end inserted into the sleeve) is magnetic. When the magnetic needle inserts into and come into contact or is getting close to the bottom of the sleeve, a magnetic field can arise outside the sleeve, thereby enabling the sleeve to attract and separate magnetic particles or biological sample with magnetic particles from the solution surrounding the sleeve. In the present embodiment, the bottom of the magnetic needle has a permanent magnet and is accordingly magnetic. In other embodiments of the present invention, the needle may become magnetic (an electromagnetic actuator) under the electromagnetic effect.

The instrument for extracting biologically active substances comprises a workbench (not shown). The workbench is disposed under the sleeve and the sleeve moving mechanism. A sample treatment area is disposed on the workbench. The sample treatment area can comprise a working area, a sample cell, a sample well, or a combination thereof. The sample treatment area is provided for disposition of the sample cell, or the sample hole for sample treatment, or for placing a vessel carrying a sample, for example, a single centrifugal tube or a single column of centrifugal tubes, a 24-well or 96-well standard cultivation plate, or alternatively, for placing non-standard cultivation plates as required. On the basis of needs and processing procedures, the sleeve can be disposed above the workbench, and can move horizontally to a specified location, move upward and downward when driven by the sleeve moving mechanism, and insert into or move out of the sample cell or the sample well disposed on the sample treatment area on the workbench for processing samples or for placing vessels containing samples. In another aspect, the workbench can be mobile, can move horizontally to a place under the sleeve on the basis of needs and processing procedures, move upward and downward when driven by the sleeve moving mechanism, and insert into or move out of the sample cell or the sample well disposed on the sample treatment area on the workbench for processing samples or for placing vessels containing samples. For example, the workbench can be controlled by a driving mechanism disposed under the workbench and can make movements in the horizontal direction.

In the embodiment illustrated by the appended drawings, the apparatus and the instrument for extracting biologically active substances provided by the present invention comprise a magnetic needle 7 and a magnetic needle moving mechanism 6. The magnetic needle moving mechanism is disposed for controlling the upward and downward movements of the magnetic needle so as the enable the same to vertically insert into and move out of the sleeve disposed under the magnetic needle.

The magnetic needle moving mechanism 6 comprises a magnetic needle bracket for securing the magnetic needle and a magnetic needle lifting mechanism for allowing the magnetic needle bracket to go upward and downward.

In the embodiment illustrated in the appended drawings, the magnetic needle bracket comprises a magnetic needle bracket end block 9 and a magnetic needle securing mechanism 8. The magnetic needle bracket end block 9 and the magnetic needle securing mechanism 8 are securely connected and make synchronous movements. In one aspect of the present invention, the magnetic needle bracket end block 9 and the magnetic needle securing mechanism 8 can be securely connected through a linkage. In the apparatus and instrument of the present invention as shown in the drawings, two pieces of linkage A 27 are used. The two ends of the two pieces of linkage A are discretely secured to the magnetic needle bracket end block 9 and the magnetic needle securing mechanism 8 by means of screws or welding.

The magnetic needle is detachably secured onto the magnetic needle securing mechanism 8. The number of magnetic needles that the magnetic needle securing mechanism is able to accommodate can be adjusted according to needs in practice, which usually is an array of 1-12 magnetic needles; and the common practice is 4, 6 or 12 magnetic needles. In another embodiment, the magnetic needle securing mechanism can secure magnetic needle arrays, each of which can have a plurality of rows of magnetic needles, for example, 24 magnetic needles (arranged in 4×6) and 96 magnetic needles (arranged in 8×12) that match cultivation plates. In the present embodiment, the bottom of the magnetic needle has a permanent magnet and is thus magnetic. In other embodiments of the present invention, the needles also can become magnetic under the electromagnetic effect.

In the embodiment illustrated by the appended drawings, the magnetic needle lifting mechanism comprises a needle propelling end block 17, a motor B 12, a screw B 32 and a screw drive pair that mates to the magnetic needle propelling end block 17, the motor drives the magnetic needle propelling end block 17 to move upward or downward through the lead screw and the screw drive pair. The magnetic needle propelling end block 17 is disposed under the magnetic needle bracket end block 9. The magnetic needle propelling end block 17 can be in contact with the magnetic needle bracket end block 9. When the motor B drives the magnetic needle propelling end block 17 to move upward through the lead screw B and the screw drive pair, the magnetic needle propelling end block 17 comes into contact with the magnetic needle bracket end block 9, and then propels the magnetic needle bracket end block 9 to move upward, thereby driving the magnetic needle securing mechanism 8 and the magnetic needle secured thereon to move upward. In the case the motor drives the magnetic needle propelling end block to move downward through the lead screw and the screw drive pair, the magnetic needle bracket end block moves downward synchronously with the magnetic needle propelling end block under the effect of gravity, thereby driving the magnetic needle securing mechanism 8 and the magnetic needle secured thereon to move downward.

In one aspect of the present invention, the magnetic needle bracket end block 9 and the magnetic needle securing mechanism 8 are disposed discretely above and under the magnetic needle propelling end block 17. The magnetic needle bracket end block 9 and the magnetic needle securing mechanism 8 are securely connected via a piece of linkage A 27 and can make synchronous movements.

The apparatus and the instrument for extracting biologically active substances further comprise a sleeve 4 and a sleeve moving mechanism 3. The sleeve moving mechanism is arranged to control upward and downward movements of the sleeve so as to enable the same to vertically insert into and move out of the sample cell or the sample well disposed on the workbench for treating samples or for placing vessels containing samples.

The sleeve moving mechanism comprises a sleeve bracket for securing the sleeve and a sleeve lifting mechanism for enable the sleeve bracket to move upward and downward.

In the embodiment illustrated by FIG. 2, the sleeve bracket of the apparatus and the instrument for extracting biologically active substances provided by the present invention comprises a sleeve bracket end block 35 and a sleeve securing mechanism 5. The sleeve bracket end block 35 and sleeve securing mechanism 5 are securely connected and can make synchronous movements. In another aspect of the present invention, the sleeve bracket end block 35 and the sleeve securing mechanism 5 can be securely connected via linkage B. In the illustrated apparatus and instrument provided by the present invention, two pieces of linkage B 28 are used; the two ends of the two pieces of linkage B are discretely secured to the sleeve bracket end block 35 and the sleeve securing mechanism 5 by means of screws or welding.

The number of sleeves that the sleeve securing mechanism is able to accommodate can be adjusted according to needs in practice. The number of sleeves can be adjusted according to needs in practice; a group usually comprises 1-12 sleeves; and the common practice is 4, 6 or 12 sleeves. In another embodiment, the sleeve securing mechanism can secure sleeve arrays, each of which can have a plurality of rows of sleeves, for example, 24 sleeves (arranged in 4×6), 96 sleeves (arranged in 8×12) or the like that match cultivation plates.

In the embodiment illustrated by the drawings, the sleeve lifting mechanism comprises a sleeve lifting end block 36, a motor A 11, a lead screw A 31 and a screw drive pair that mates to the sleeve lifting end block 36, the motor drives the sleeve lifting end block 36 to move upward or downward through the lead screw and the screw drive pair. The sleeve lifting end block 36 is disposed under the sleeve bracket end block 35. The sleeve lifting end block 36 can get into contact with the sleeve bracket end block 35. When the motor A drives the sleeve lifting end block 36 to move upward through the lead screw B and the screw drive pair, the sleeve lifting end block 36 can come into contact with the sleeve bracket end block 35, and push the sleeve bracket end block 35 to move upward, thereby driving the sleeve securing mechanism 5 and the sleeve secured thereon to move upward. In the case the motor A drives the sleeve lifting end block to move downward through the lead screw and the screw drive pair, the sleeve bracket end block moves downward synchronously with the sleeve lifting end block under the effect of gravity, thereby driving the sleeve securing mechanism and the sleeve secured thereon to move downward.

Figures 1, 3:
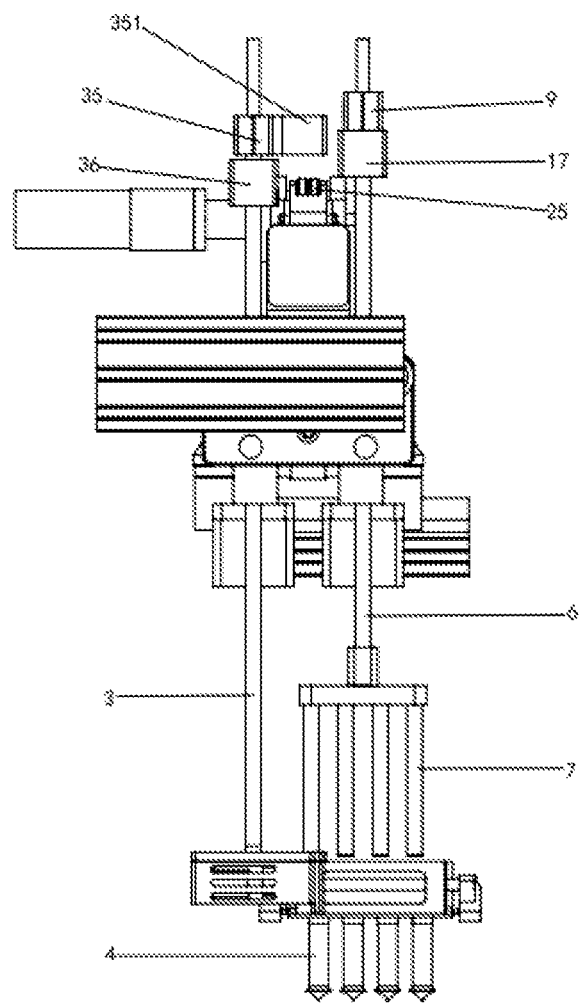
Figures 2, 3:
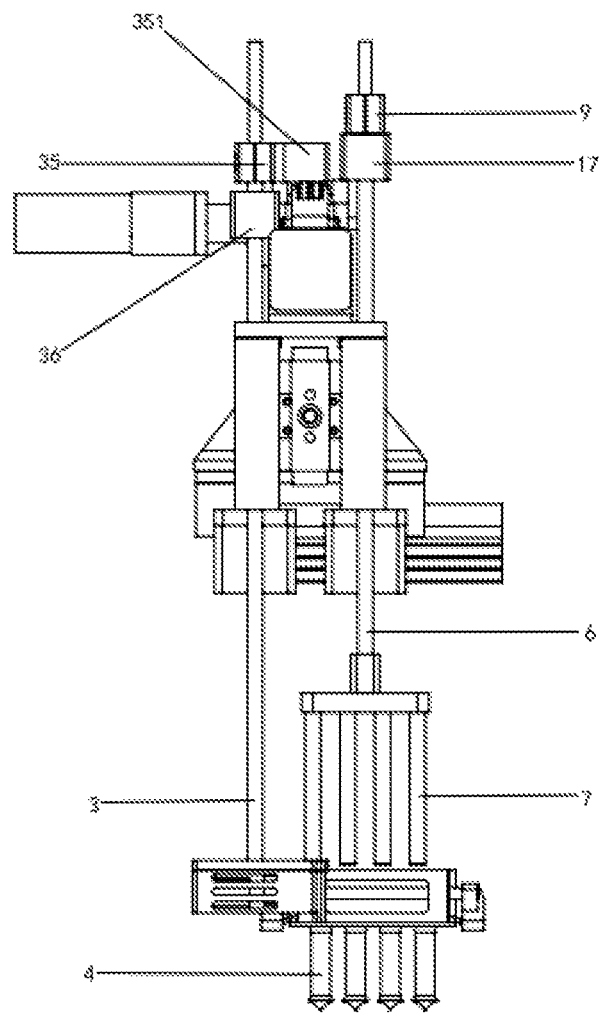
Figure 4:
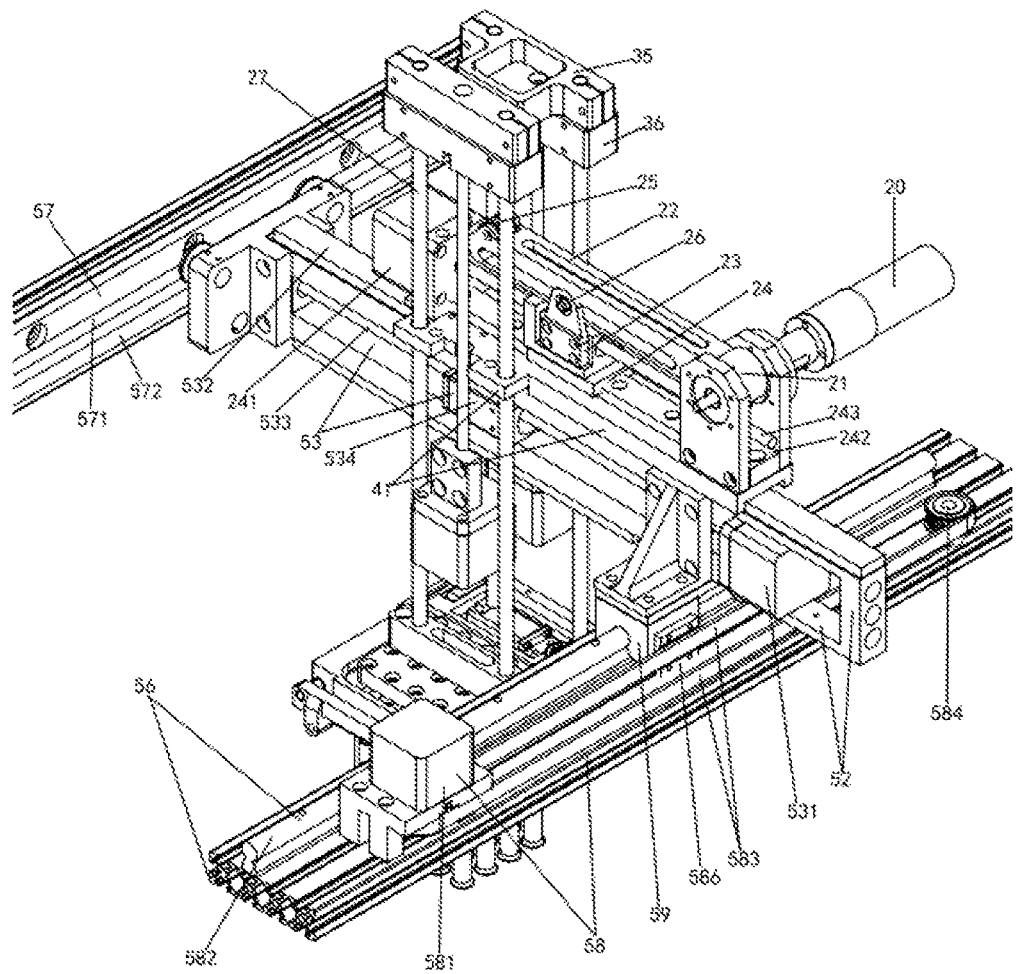
FIG. 4 is a side cross-sectional schematic view of a preferred embodiment of the present invention.

In the present invention, the sleeve moving mechanism 3 also can be in contact with the vibration mechanism 19, so that the vibrations output by the vibration mechanism 19 enables the sleeve moving mechanism to make upward and downward vibrations, thereby driving the sleeve securing mechanism 5 and the sleeve secured thereon to make upward and downward vibrations. In one aspect of the present invention, the sleeve moving mechanism can be in contact with the vibration mechanism 19 via the sleeve bracket, for example, it is viable to arrange the sleeve bracket end block 35 in contact with the vibration output member of the vibration mechanism 19. In the preferred embodiment as illustrated, the sleeve bracket end block 35 is in a triangle shape, wherein the protruding portions 351 can be in contact with the vibration outputting member (i.e. the vibration wheel 25) of the vibration mechanism (as shown in FIG. 3-2 and FIG. 4). When the vibration wheel starts vibration, it propels the sleeve bracket end block, which accordingly drives the sleeve to make upward and downward vibrations. The bottom block 352 of the triangleshaped sleeve bracket end block can be in contact with the sleeve lifting end block 36, and can make upward and downward vibrations under driving from the sleeve lifting end block 36.

FIG. 3-1 and FIG. 3-2 are side cross-sectional views of the apparatus and the instrument for extracting biologically active substances. As shown, the sleeve lifting end block 36 and the sleeve bracket end block 35 are separable, which accordingly allows vibrations and upward and downward movements of the sleeve to be independently controlled by different mechanisms.

The sleeve lifting end block 36 is disposed under the sleeve bracket end block 35. When the motor drives the sleeve lifting end block 36 to move upward through the lead screw and the screw drive pair, the sleeve bracket end block 35 is propels to move upward, thereby driving the sleeve securing mechanism 5 and the sleeve secured thereon to move upward. When the motor drives the sleeve lifting end block 36 to move downward through the lead screw and the screw drive pair, the sleeve bracket end block moves downward synchronously with the sleeve lifting end block under the effect of gravity, thereby driving the sleeve securing mechanism 5 and the sleeve secured thereon to move downward.

In the apparatus and the instrument for extracting biologically active substances illustrated in the preferred embodiment, the sleeve lifting end block is disposed under the sleeve bracket end block, the length and width of its upper surface is equal to the lower surface of the bottom block 352 of the sleeve bracket end block, which can hold and propel the sleeve lifting end block.

In the apparatus and the instrument for extracting biologically active substances illustrated in the preferred embodiment, the sleeve bracket end block 35 is in a T-shape, whose protruding portions 351 can be in contact with the vibration output member (i.e. the vibration wheel 25) of the vibration mechanism.

In addition, as shown in the drawings, the magnetic needle propelling end block 17 and the magnetic needle bracket end block 9 are separable. When the motor drives the propelling end block to move upward through the lead screw and the screw drive pair, the magnetic needle bracket is propelled to move upward by the magnetic needle bracket end block. This enables the magnetic needle to move upward so as to move out of the sleeve. The magnetic needle bracket moves downward under the effect of gravity. The magnetic needle propelling end block and the magnetic needle bracket of the instrument provided by the present invention are separable. This design can allow sufficiently close contact between the magnetic needle end and the bottom of the sleeve, reduces the requirements for the electrical control, and can prevent occurrence of the magnetic needle colliding with the bottom of the sleeve.

FIG. 3-1 shows the condition of the apparatus and the instrument when the sleeve is in the non-vibrating working state. The sleeve lifting end block 36 can move upward to come into contact with the sleeve bracket end block 35 and propels the sleeve bracket end block 35 to move upward, but has no contact with the vibration mechanism 19. Specifically, the protruding portions 351 of the sleeve bracket end block 35 have no contact with the vibration output member (i.e. the vibration wheel 25) of the vibration mechanism.

In this case, when it is necessary to insert the magnetic needle 7 into the sleeve 4 to generate magnetism at the bottom of the sleeve for attracting magnetic particles or biological samples with magnetic particles outside the sleeve, the magnetic needle propelling end block 17 moves downward and the magnetic needle bracket end block 9 also moves downward under the effect of gravity; accordingly, the magnetic needle moving mechanism 6 and the magnetic needle 7 secured thereon move downward to insert into the sleeve and reach the pre-determined position that is closest to the bottom of the sleeve 4. The pre-determined position where the magnetic needle end comes closest to the bottom of the sleeve can be defined through arrangement of the magnetic needle moving mechanism 6 and the sleeve moving mechanism 3, for example, the arrangement can be that the bottom of the magnetic needle securing mechanism is in contact with the top of the sleeve securing mechanism, or the bottom of the magnetic needle securing mechanism is in contact with the protruding member disposed on the top of the sleeve securing mechanism; the protruding member can be made of a buffer material.

On the other hand, when it is necessary to take the magnetic needle 7 out of the sleeve 4 to remove magnetism from the bottom of the sleeve for releasing the magnetic particles or biological samples with magnetic particles outside the sleeve, the magnetic needle propelling end block 17 moves upward to push the magnetic needle bracket end block 9 to move upward, accordingly the magnetic needle bracket and the magnetic needle secured thereon move upward and out of the sleeve.

FIG. 3-2 illustrates the working state when the sleeve makes vibrations.

When it becomes necessary for the sleeve to rinse off the magnetic particles or biological samples with magnetic particles attracted around the sleeve through vibrations, the magnetic needle bracket end block pushes the magnetic needle bracket to move upward, so the magnetic needle goes up to get out the sleeve. Then, the sleeve bracket starts vibrations under the effect of the vibration mechanism.

Wherein, the sleeve lifting end block 36 move downward till the sleeve bracket end block 35 comes into contact with the vibration mechanism 19, which specifically means the protruding portion 351 of the sleeve bracket end block 35 coming into contact with the vibration output member (i.e. the vibration wheel 25) of the vibration mechanism. The sleeve lifting end block 36 moves continuously downward, so that the sleeve lifting end block 36 is separated from the sleeve bracket end block 35. When the vibration wheel 25 starts vibrations, it propels the sleeve bracket end block 35, and this accordingly drives the sleeve moving mechanism 3 and the sleeve 4 to make upward and downward vibrations.

The apparatus and the instrument for extracting biologically active substances provided by the present invention comprise a bracket 13 for holding the magnetic needle moving mechanism and the sleeve moving mechanism. The bracket is capable of holding the magnetic needle moving mechanism and the sleeve moving mechanism of the apparatus and the instrument provided by the present invention, so as to enable the inside of the instrument to stay perpendicular and suspended. The bracket may comprise supporting posts and a bracket ceiling. In the apparatus and the instrument for extracting biologically active substances of the preferred embodiment as illustrated, the bracket 13 comprises a bracket ceiling 41 and supporting posts 42. In the apparatus and the instrument for extracting biologically active substances of the preferred embodiment, the supporting posts 42 comprises 4 rectangular securing blocks, whose tops are discretely secured to the bracket ceiling 41 by means of, for example, screws or welding. The four rectangular securing blocks can be one cast or two casts, each of which is composed of two rectangular securing blocks, or alternatively, can be individual parts that are secured with each other by means of connecting members or welding. For example, as shown in FIG. 1 and FIG. 2, the apparatus and the instrument for extracting biologically active substances of the preferred embodiment comprise a front securing block 421 and a rear securing block 422, wherein the rear securing block 422 comprises two rectangular securing blocks 4221 and 4222, and a post side wall 4223 between the two rectangular securing blocks. The securing block 421 on the other end also has the same structure. Preferably, connecting members are also disposed at the bottoms of the four rectangular securing blocks to secure each other.

As shown, the bracket ceiling 41 and the supporting posts 42 comprise through-holes, including the through-holes 43 on the bracket ceiling and the through-holes on the supporting posts situated under the bracket ceiling, as shown. The through-hole can accommodate passing through of the linkage A 27 that connects the magnetic needle bracket end block 9 and the magnetic needle securing mechanism 8 and the passing through of the linkage B 28 that connects the sleeve bracket end block 35 and the sleeve securing mechanism 5. Additionally, as shown, through-holes are also disposed on two sides of the magnetic needle propelling end block 17 and the sleeve lifting end block 36. As shown in FIG. 1, two pieces of linkage A 27 movably pass through the magnetic needle bracket end block 9, the magnetic needle propelling end block 17, the bracket ceiling 41 and the through-holes of the supporting posts 42. Accordingly, the bracket 13 also functions to restrict and secure the magnetic needle bracket end block 9 and the magnetic needle propelling end block 17, namely, to restrict and secure the magnetic needle bracket and the magnetic needle moving mechanism. Likewise, as shown in FIG. 2, a piece of linkage B 28 movably passes through the sleeve bracket end block 35, the sleeve lifting end block 36, the bracket ceiling 41 and the through-holes of the another two supporting posts 42. Accordingly, the bracket 13 also functions to restrict and secure the sleeve bracket end block 35 and the sleeve lifting end block 17, namely, to restrict and secure the sleeve bracket and the sleeve moving mechanism.

The bracket 13 of the apparatus and the instrument for extracting biologically active substances provided by the present invention can be secured inside the instrument through beams connected with side walls of the housing or through columns disposed at the bottom of the instrument, and suspended over the workbench, so as to enable the sleeve and the magnetic needle to be vertically suspended over the sample cell or the sample well or disposed on the workbench for sample treatment or for placing vessels containing samples. In one aspect of the present invention, the beams can be lateral beams independent from the bracket ceiling 41 of the bracket of the apparatus and the instrument. In another aspect of the present invention, the beams can be the bracket ceiling 41 of the bracket, two ends of which can extend to the side walls of the housing to form a beam thereby being secured over the workbench. As described hereinafter, in another aspect of the present invention, the beam can be the bracket 52 of the X axis moving mechanism, the two ends of which can extend to the side walls of the housing to form a beam thereby being secured over the workbench; the bracket ceiling 41 of the bracket 13 is securely connected with the beam, i.e. the bracket 52 of the X axis moving mechanism.

FIG. 4 shows the view of the internal structure of the apparatus and the instrument for extracting biologically active substances given in the preferred embodiment of the present invention. The structure of the apparatus and the instrument shown in FIG. 4 does not include the front securing block 421 of the support post 42.

The apparatus and the instrument for extracting biologically active substances provided by the present invention further comprise a vibration mechanism, which is capable of generating vibrations and transmitting the same to the sleeve moving mechanism, so as to enable the sleeve moving mechanism to drive the sleeve to make upward and downward vibrations. The sleeve of the apparatus and the instrument for extracting biologically active substances provided by the present invention can make vibrations at a frequency as high as 20 Hz.

The vibration mechanism provided by the present invention comprises a lever bar, a movable fulcrum and an eccentric mechanism, and the movable fulcrum can move along the lever bar. One of the processing step in the operation of the apparatus and the instrument for extracting biologically active substances provided by the present invention requires the magnetic needle and sleeve to make rapid upward and downward vibrations. According to different job requirements, vibrations are required to have different amplitudes and frequencies. The arrangement of the vibration mechanism of the apparatus and the instrument for extracting biologically active substances provided by the present invention allows the amplitude and the frequency of the vibrations to be adjustable, yet the starting points of the amplitudes (the peak negative point) are the same regardless of adjustment to the amplitudes; this accordingly can protect the mechanisms such as the sleeve and, with other features of the present invention, allow the apparatus and the instrument provided by the present invention to exhibit such advantages as small noise and long service life.

As shown in FIG. 1, FIG. 2 and FIG. 4, the vibration mechanism of the present invention comprises a linear lever bar 22, a movable bracket 23, a movable fulcrum 26, a driving mechanism 24 for driving the movable bracket, a vibration wheel 25 for transmitting vibrations to the sleeve through getting into contact with the sleeve lifting mechanism (via the sleeve bracket end block 35), an eccentric wheel 21 and an eccentric wheel driving motor 20. The lever bar is linear and has a hollow slot parallel to its upper and lower edges. The movable bracket driving mechanism is composed of a movable bracket motor 241, a linear rail 242, a lead screw 243 and a screw drive pair connected with the movable bracket 23. The movable fulcrum passes through the hollow slot of the lever bar and can move inside the hollow slot along the direction of the lever bar when it is driven by the movable bracket driving mechanism, thereby forming the movable fulcrum of the lever. The vibration wheel 25 that transmits vibrations via getting into contact with the sleeve bracket end block 35 of the sleeve lifting mechanism and the eccentric wheel are situated discretely at the two ends of the movable fulcrum. The eccentric wheel is in contact with the lever bar; when the eccentric wheel turns, it causes the lever bar (effort arm) on the side of the eccentric wheel against the fulcrum to make translation, and the lever bar (resistance arm) on the other side of the fulcrum and the vibration wheel then synchronously make translation to the opposite direction, namely, the lever bar turns around the fulcrum. The rotation of the eccentric wheel causes the vibration wheel to vibrate, so as to enable the sleeve moving mechanism to drive the sleeve to make upward and downward vibrations. That is, in the vibration mechanism of the apparatus and the instrument for extracting biologically active substances provided by the present invention, the eccentric mechanism (eccentric wheel in the embodiment) is provided for generating vibrations and controlling the frequency rates. The amplitude values can be controlled via translating the position of the movable fulcrum on the lever or, alternatively, in combination with the rotating mode of the eccentric wheel.

In the apparatus and the instrument shown in the embodiment of the present invention, the wheel rim of the eccentric wheel is in direct contact with the linear lever bar, the minimum radius of the eccentric wheel (i.e. the minimum distance from its axis to its rim) is equal to the distance from the axis of the eccentric wheel to the lever bar; the radius direction of the minimum radius of the eccentric wheel is perpendicular to the moving direction of the movable fulcrum (i.e. that of the lever bar) of the lever; in this case, no matter how the fulcrum moves inside the hollow slot of the lever bar, the vibration wheel always situates at the point of peak negative amplitude when the eccentric wheel comes into contact with the lever bar at the minimum radius point. No matter how the turning speed of the eccentric wheel changes or how the position of the movable fulcrum changes on the lever bar (namely, regardless of the change to the amplitude and frequency of the vibration wheel), the peak negative point of the vibration wheel does not change, that is, the lowest point at which the sleeve vibrates does not change.

In other embodiments of the present invention, the eccentric wheel also can be replaced by an eccentric cam to realize the objectives of the present invention.

By use of the aforesaid vibration mechanism, the apparatus and the instrument for extracting biologically active substances provided by the present invention can allow random adjustment to the vibration frequency and amplitude at the meantime of keep the peak negative point of various amplitudes unchanged regardless of adjustment to the amplitudes; this can largely expand the range of adjustment to the vibration frequency and accordingly enable the whole apparatus and the instrument to exhibit advantages as small noise and long service life.

In one aspect of the present invention, the vibration mechanism is disposed above the mechanism bracket 13. Take the preferred embodiment of the present invention as an example. As shown, the vibration mechanism is amounted on the top of the bracket ceiling 41 and is securely connected with the bracket ceiling by means of screws or welding, for example, it can be securely connected with the bracket ceiling through the stand base of its driving mechanism 24 by means of screws. Accordingly, the vibration mechanism 19 makes synchronous movements when the magnetic needle moving mechanism 6 and the sleeve moving mechanism move in the horizontal direction along the X axis and the Y axis. Through the arrangement of the vibration mechanism above the mechanism bracket 13, the apparatus and the instrument of the present invention exhibit such advantages as having a compact structure, easy for maintenance, making only small noise, having a long service life and having a low manufacturing cost.

The magnetic needle moving mechanism and the sleeve moving mechanism in the apparatus and the instrument provided by the present invention can move in the horizontal direction along the X axis and the Y axis that are perpendicular to each other. In one aspect of the present invention, the use of the positioning mechanism 14 allows the magnetic needle moving mechanism and the sleeve mechanism and the vibration mechanism to make movements in the horizontal direction along the X axis and the Y axis.

An X axis positioning mechanism comprises an X axis bracket and an X axis movement driving mechanism. The X axis can be used to connect and hold the magnetic needle moving mechanism and the sleeve movement mechanism. The X axis can further be used to connect and support the X axis movement driving mechanism. In the instrument of a preferred embodiment as shown, the X axis bracket 52 is a rectangular frame, whose longitudinal direction is same as the layout direction of the bracket ceiling 41. The bracket ceiling 41 of the bracket 13 is disposed on the top of the X axis bracket 52 and can be secured to the bracket 52 by means of screws or the like. The X axis movement driving mechanism 53 comprises an X axis movement motor 531, a linear rail 532, a lead screw 533 and a screw drive pair 534 connected with the bracket 13. The linear rail 532 is disposed at the top of the X axis bracket 52, and the bracket ceiling 41 of the bracket 13 can connect with the linear rail 532 through sliding fit. The front securing block 421 of the mechanism bracket 13 (not shown in FIG. 4) and the rear securing block 422 are discretely disposed at the two ends of the X axis bracket 52. The screw drive pair 534 can be secured to the mechanism bracket 13 by means of screws or the like, for example, it can be secured with the front securing block 421 and the rear securing block 422 of the mechanism bracket 13. Accordingly, the movements along the X axis direction made by the screw drive pair 534 under the driving from the motor can drive the bracket 13 to make synchronous movement along the X axis direction, and accordingly drive the magnetic needle and the magnetic needle moving mechanism, the sleeve and the sleeve moving mechanism, the vibration mechanism to make synchronous movement in the X axis direction.

In another aspect of the present invention, the provision of the bracket 52 of the X axis moving mechanism can be used to support or hold the beams of the magnetic needle moving mechanism and the sleeve moving mechanism and the bracket 13 of the instrument provided by the present invention. The two ends of the bracket 52 of the X axis moving mechanism can extend to the side walls of the housing to form a beam, and thereby being secured over the workbench.

The Y axis positioning mechanism comprises a Y axis bracket and a Y axis movement driving mechanism 58. The Y axis can be used to connect and support the needle moving mechanism and the sleeve moving mechanism. The Y axis can further be used to hold and secure the Y axis movement driving mechanism.

In the instrument of a preferred embodiment of the present invention as shown, the Y axis bracket comprises a left bracket 56 and a right bracket 57.

The left bracket 56 comprises a supporting panel 561. In addition, the Y axis movement driving mechanism 58 is disposed on the left bracket 56. The Y axis movement driving mechanism 58 comprises a Y axis movement motor 581, a Y axis movement sliding rail 582, a conveyor belt 583, an upper belt pulley 584 and a lower belt pulley, a link slider 59 for connecting and securing the bracket 13, and a conveyor belt securing member 586 that is securely connected with the link slider 59. The link slider 59 can be directly or indirectly connected and secured to the bracket 13. In one aspect of the present invention, the link slider 59 can be securely connected to the X axis bracket 52 by means of screws or the like; the X axis bracket is arranged to move synchronously with the bracket 13 along the Y axis. The slider rail 582 and the link slider 59 are connected through sliding fit. The conveyor belt 583 engages the teeth of the upper belt pulley 584 and the lower belt pulley (not shown). When driven by the Y axis movement motor 581, the teeth of the upper belt pulley 584 and the lower belt pulley convey effort to the conveyor belt 583 and the conveyor belt securing member 586, which accordingly via the link slider 59 drives the X axis bracket 52 to make lateral movement along the direction of the Y axis. Since the X axis bracket 52 makes synchronous movement along the Y direction with the magnetic needle moving mechanism and the sleeve moving mechanism, this accordingly enables the magnetic needle moving mechanism and the sleeve moving mechanism to make lateral movement along the Y direction.

The right bracket 57 of the Y axis bracket has a supporting panel 571 and a sliding rail and can hold the bracket 52 of the X axis movement mechanism and enables the bracket to make movement in the horizontal direction. In the apparatus and the instrument of the preferred embodiment of the present invention as shown in the drawings, a roller 54 is disposed at the side of the bracket 52 of X axis movement mechanism that is in contact with the right bracket 57 of the Y axis bracket, and the roller can roll along the sliding rail 572 of the right bracket 57; this accordingly allows the bracket 52 to make movement in the horizontal direction on the side that is in contact with the right bracket 572.

The supporting panels of the left bracket 56 and the right bracket 57 of the Y axis bracket can be individually secured to the bracket or beam inside the housing of the instrument by means of screws or welding, thereby forming such a structure, for example a beam, that is capable of supporting or holding the magnetic needle moving mechanism, the sleeve moving mechanism and other mechanism such as the bracket of the apparatus and the instrument provided by the present invention.

In one aspect of the present invention, the two ends of the bracket 52 of the X axis movement mechanism can extend to the sidewalls of the housing or to form a beam with the supporting panels of the Y axis bracket for supporting the bracket 13 and enabling the sleeve and the magnetic needle to be perpendicularly suspended over the workbench.

A person of ordinary skills in the art can realize the functions of the positioning mechanism 14 of the apparatus and the instrument of the present invention by various means commonly known in the art, namely, the function of enabling the magnetic needle moving mechanism and the sleeve moving mechanism to make lateral movements along the X axis and the Y axis that are perpendicular to each other.

Although the exemplary embodiments and their advantages have been described at length herein, it should be understood that various alternations, substitutions and modifications may be made to the embodiments without departing from the spirit of the present invention and the scope as defined by the appended claims. As for other examples, it may be easily appreciated by a person of ordinary skill in the art that the order of the process steps may be modified without departing from the scope of the present invention.

In addition, the scope, to which the present invention is applied, is not limited to the process, mechanism, manufacture, material composition, means, methods and steps described in the specific embodiments in the specification. According to the disclosure of the present invention, a person of ordinary skill in the art should readily appreciate from the disclosure of the present invention that the process, mechanism, manufacture, material composition, means, methods and steps currently existing or to be developed in future, which perform substantially the same functions or achieve substantially the same as that in the corresponding embodiments described in the present invention, may be applied according to the present invention. Therefore, it is intended that the scope of the appended claims of the present invention includes these process, mechanism, manufacture, material composition, means, methods or steps.

What is claimed is:

1. An apparatus for extracting biologically active substances comprising:
    a magnetic needle (7) and a magnetic needle moving mechanism (6); the magnetic needle moving mechanism comprises a magnetic needle bracket and a magnetic needle lifting mechanism, and the magnetic needle is detachably secured onto the magnetic needle bracket;
    a sleeve (4) and a sleeve moving mechanism (3); the sleeve moving mechanism comprises a sleeve bracket and a sleeve lifting mechanism, and the sleeve is detachably secured on the sleeve bracket; wherein, upward and downward movements of the sleeve lifting mechanism enable the sleeve to vertically insert into and move out of a sample treatment area; additionally, the sleeve moving mechanism is capable of making upward and downward vibrations;
    a bracket (13) for holding the magnetic needle moving mechanism (6) and the sleeve moving mechanism (3); and
    a vibration mechanism (19) capable of generating and outputting vibrations so as to enable the sleeve moving mechanism (16) to make upward and downward vibrations; wherein the vibration mechanism comprises a lever bar, a movable fulcrum and a rotary mechanism; wherein the rotary mechanism has a wheel and an axis; when the rotary mechanism turns around the axis, the outer rim of its wheel can push the lever bar to turn around the movable fulcrum, thereby generating vibrations; wherein the vibration mechanism is disposed above the bracket (13),
    wherein, upward and downward movements of the magnetic needle lifting mechanism enable the magnetic needle to vertically insert into and move out of the sleeve.

2. The apparatus according to claim 1, wherein the arrangement of the lever bar, the movable fulcrum and the rotary mechanism is such that, under the working state, changes of the position of the movable fulcrum are restricted to be the position of negative peak amplitude, which refers to the position of the fulcrum of the vibration mechanism when the closest rim point of the rotary mechanism of said vibration mechanism exerts a propelling effect on the lever bar.

3. The apparatus according to claim 1, wherein the rotary mechanism is an eccentric rotary mechanism whose axis is off the centre.

4. The apparatus according to claim 1, wherein the movable fulcrum is a movable fulcrum capable of moving along the lower edge of the lever bar or a movable fulcrum moving in a groove or a hollow slot disposed on the lever bar.

5. The apparatus according to claim 4, wherein the wheel comprises an eccentric wheel.

6. The apparatus according to claim 1, wherein the lever bar is a linear lever bar.

7. The apparatus according to claim 1, wherein the lever bar comprises a linear lever bar (22); and the movable fulcrum can move along the lever bar in the direction of the axis direction of the lever bar, wherein the outer rim of the eccentric wheel is in contact with the lever bar, and its minimum radius is equal to the distance from its axis to the lever bar.

8. The apparatus according to claim 7, wherein the movable fulcrum comprises a mobile bracket (23), a mobile bracket driving mechanism (24) and a movable fulcrum axis (37); wherein the lever bar comprises a hollow slot parallel to its upper surface, the movable fulcrum axis goes through the hollow slot and moves inside the hollow slot under driving from the mobile bracket driving mechanism to form the movable fulcrum of the lever.

9. The apparatus according to claim 1, wherein the lever bar comprises a vibration wheel (25), which is in contact with the sleeve moving mechanism for conveying vibrations; the vibration wheel and the rotary mechanism are situated on two sides of the movable fulcrum.

10. The apparatus according to claim 1, wherein the bracket (13) comprises a bracket ceiling (41) and supporting posts (42), wherein the vibration mechanism is disposed above the bracket ceiling (41).

11. The apparatus according to claim 1, wherein the magnetic needle bracket comprises a magnetic needle bracket end block (9) and a magnetic needle securing mechanism (8), wherein the magnetic needle is detachably secured on the magnetic needle securing mechanism; the magnetic needle lifting mechanism comprises a needle propelling end block (17) disposed under the magnetic needle bracket end block; when the magnetic needle propelling end block moves upward, it propels the magnetic needle bracket end block to move upward, thereby propelling the magnetic needle bracket to move upward.

12. The apparatus according to claim 1, wherein the sleeve bracket comprises a sleeve bracket end block (35) and a sleeve securing mechanism (5), wherein the sleeve is detachably secured on the sleeve securing mechanism; the sleeve lifting mechanism comprises a sleeve lifting end block (36) disposed under the sleeve bracket end block (35); when the sleeve lifting end block moves upward, it propels the sleeve bracket end block to move upward, thereby propelling the sleeve bracket to move upward; when the sleeve lifting end block moves downward, the sleeve bracket end block makes synchronous downward movement with the sleeve lifting end block under the effect of gravity.

13. The apparatus according to claim 1, wherein the sleeve bracket is in contact with the vibration mechanism (19); vibrations generated by the vibration mechanism enables the sleeve bracket to make upward and downward vibrations.

14. The apparatus according to claim 13, wherein the sleeve bracket comprises a sleeve bracket end block (35), and wherein the sleeve bracket end block is in contact with a vibration wheel (25) of the vibration mechanism (19) for conveying vibrations.

15. The apparatus according to claim 1, further comprising a positioning mechanism (14) that enables the magnetic needle moving mechanism (6) and the sleeve moving mechanism (3) to move in the horizontal direction along the X axis and the Y axis; wherein the positioning mechanism (14) comprises an X axis positioning mechanism and a Y axis positioning mechanism.

16. The apparatus according to claim 15, wherein the X axis positioning mechanism comprises an X axis bracket (52) and an X axis movement driving mechanism (53), wherein the X axis movement mechanism (53) comprises an X axis movement motor (531), a linear rail (532), a lead screw (533) and a screw conveyor member (534) that is connected to the bracket (13); wherein the linear rail (532) is disposed on the top of the X axis bracket (52), the bracket ceiling (41) of the bracket (13) is connected with the linear rail (532) through sliding fit, and the screw conveyor member is secured to the mechanism bracket (13).

17. The apparatus according to claim 15, wherein the Y axis positioning mechanism comprises a Y axis bracket and a Y axis movement driving mechanism (58), wherein the Y axis movement mechanism (58) comprises a Y axis movement motor (581), a Y axis mobile sliding rail (582), a conveyor belt (583) and an upper belt pulley (584) and a lower belt pulley; a link slider (59) for establishing connection with the bracket (13); a conveyor securing member (586) that is securely connected to the link slider (59), the sliding rail (582) is connected with the link slider (59) through sliding fit, and the conveyor belt (583) engages teeth of the upper belt pulley (584) and the lower belt pulley.

18. The apparatus according to claim 1, wherein the magnetic needle is made of a permanent magnetic material, and the sleeve is made of a non-magnetic material.

19. An instrument for extracting biologically active substances comprising:
a housing,
a workbench on which a sample treatment area is disposed; and the apparatus for extracting biologically active substances according to claim 1.

* * * * *